United States Patent [19]

Steidley

[11] 4,022,258

[45] May 10, 1977

[54] PORTED CLOSURE AND CONNECTOR THEREFOR

[75] Inventor: Roy B. Steidley, Ellington, Conn.

[73] Assignee: American Hospital Supply Corporation, Evanston, Ill.

[22] Filed: Oct. 28, 1975

[21] Appl. No.: 626,201

[52] U.S. Cl. .............................. 141/330; 215/250; 222/81

[51] Int. Cl.² ........................................ B65D 41/50

[58] Field of Search ................ 215/247, 250, 253; 222/81, 83, 89; 141/330, 329; 128/272.3

[56] References Cited

UNITED STATES PATENTS

| 3,156,369 | 11/1964 | Bowes | 215/250 X |
| 3,580,423 | 5/1971 | Gilman | 222/81 |
| 3,831,814 | 8/1974 | Butler | 222/81 |
| 3,938,520 | 2/1976 | Scislowicz | 141/330X |

Primary Examiner—Donald F. Norton
Attorney, Agent, or Firm—Tilton, Fallon, Lungmus, Chestnut & Hill

[57] ABSTRACT

A dual-purpose one-piece plastic closure for surgical irrigation fluid containers. The closure may be removed from the neck of the container when liquid is to be dispensed by pouring or, alternatively, may be pierced by and sealingly coupled to the connector spike of an irrigation set when liquid is to be drained from the container for closed system irrigation. The closure includes a port sleeve which has a primary seaing zone at a level slightly below the closure's top wall. The disclosed embodiment also includes a secondary sealing zone between the primary zone and the dome-shaped bottom wall of the port sleeve. The connector spike, its construction, and its cooperative relationship with the closure, are also disclosed.

24 Claims, 9 Drawing Figures

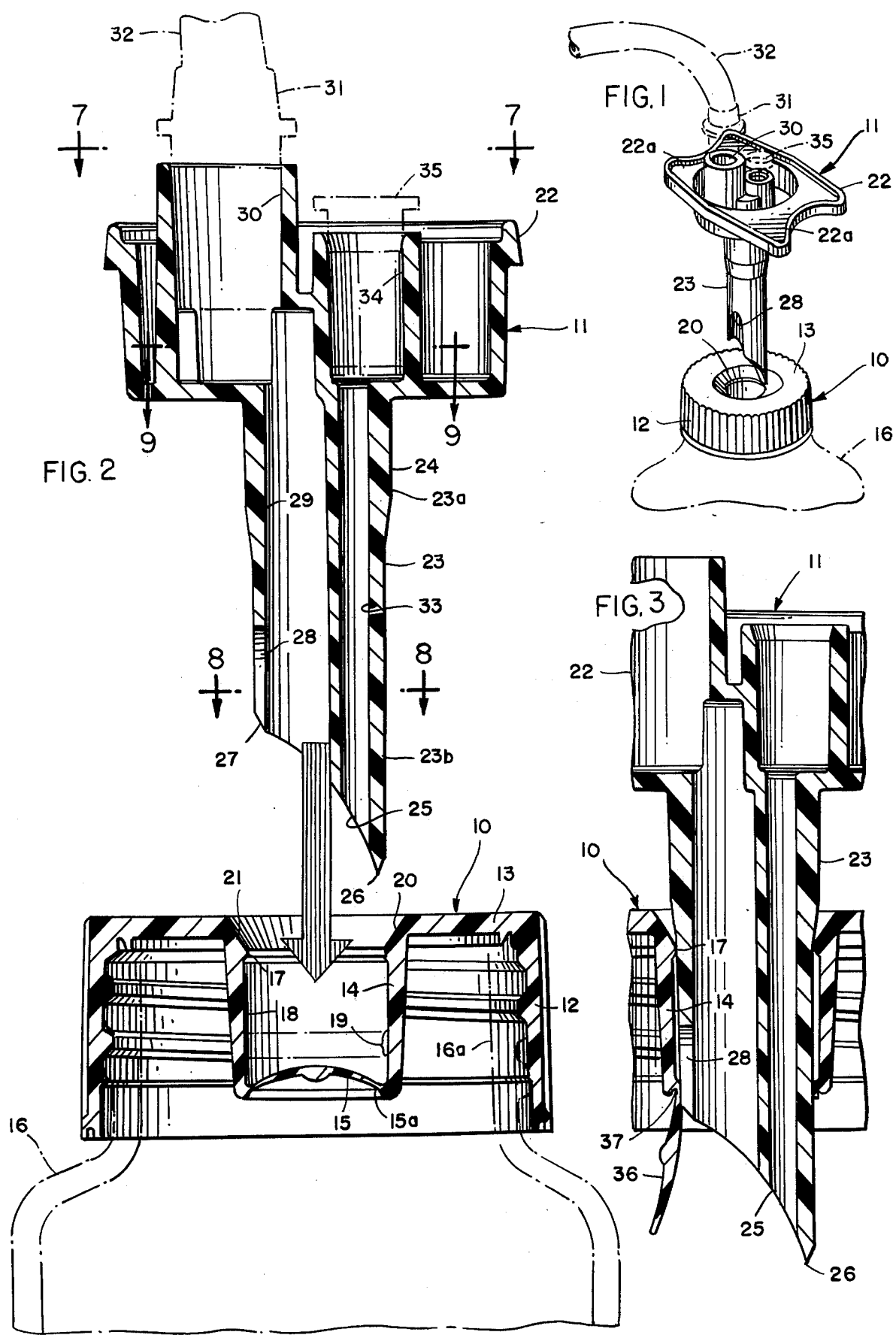

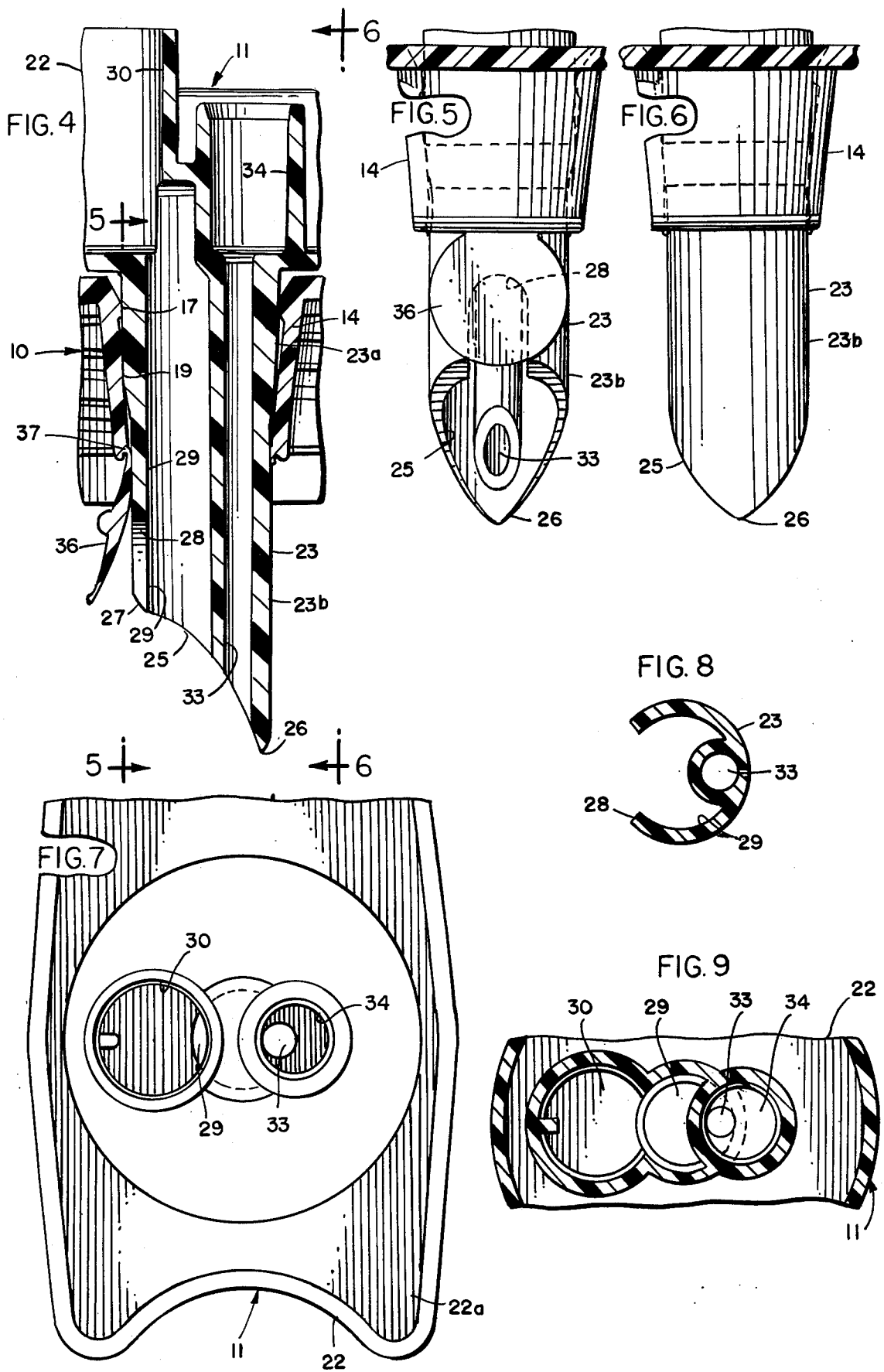

PORTED CLOSURE AND CONNECTOR THEREFOR

BACKGROUND AND SUMMARY

Sterile irrigating fluids, commonly consisting of distilled water, normal saline, or physiological solutions of sorbitol or glycine, are widely used for post-operative irrigation, for flushing wounds and body passages, cavities, and other areas undergoing surgical examination or operation. For example, continuous or intermittent irrigation is commonly required during transurethral prostatic resections and for cystoscopic examinations. Surgical apparatus particularly suitable for irrigation in transurethral resections is disclosed in co-owned U.S. Pat. No. 3,677,248.

The manner of administration of such irrigating fluids depends on the type of examination or treatment involved and particularly on the quantities of fluid required. Relatively large quantities are frequently needed for flushing purposes and, in those cases, the surgeon or assistant may simply remove the closure and pour the fluid directly from the bottle. In other instances, as where a stream of irrigating liquid is to be directed through a cystoscope or resectoscope, the instrument is attached to the flexible tubing of an administration set with the connector of that set being secured to the bottle in place of its original closure.

Administration sets for irrigation fluids are available with different forms of bottle connectors but each form has some shortcomings in terms of cost, inconvenience of use, and/or possible risks of fluid contamination. For example, one connector takes the form of a threaded cap to which the flexible tubing of the administration set is permanently secured. Substitution of that cap for the original threaded bottle cap obviously requires considerable manipulation and time. In another arrangement, the connector comprises a plug which need only be inserted into the mouth of the bottle; however, such a procedure still requires prior removal of the bottles's original cap.

One aspect of this invention therefore lies in providing a dual-purpose closure for an irrigation bottle and, specifically, a closure which constitutes the original closure of the bottle, which is to be left in place when the irrigating fluid is to be administered through an administration set, and which is to be removed only if circumstances require that fluid be poured from the bottle. While it is recognized that closures with pierceable membranes are widely used for intravenous administration of blood and parenteral fluids, such closures are ordinarily secured against removal (see, for example, U.S. Pat. No 2,730,097) and would be clearly unsuitable for use in the administration of irrigation solutions for that reason alone and also because of their relatively expensive, ordinarily multiple-piece, construction.

This invention is concerned with a relatively simple, inexpensive one-piece molded plastic closure which functions as the original closure for the bottle of surgical irrigation fluid and which is readily unthreaded from the bottle when fluid is to be poured from that bottle. When instead the fluid is to be drained through an administration set, the imperforate closure is left in place and the connector of the administration set is frictionally coupled to the closure with a hollow spike portion of the connector piercing a wall portion of the closure. Thus, either closure removal or administration set attachment may be easily and quickly accomplished — advantages which are particularly important in the surgical field where any delays may have serious consequences.

The one-piece closure is formed of semi-rigid plastic and has a generally cylindrical side wall, an annular top wall, a tubular sleeve communicating with the central opening of the top wall, and a bottom wall closing the lower end of the sleeve. Within the sleeve, at a level just below the top wall, is an annular rib which projects into the cavity of the sleeve and which provides a primary sealing zone for slidably and sealingly engaging the outer surface of a connector spike insertable into the sleeve to pierce the bottom wall of that sleeve and to place the interior of the irrigation bottle in flow communication with an administration set. In the disclosed embodiment, the sleeve is downwardly tapered and has along its inside surface a secondary sealing zone spaced between the primary zone and the bottom wall of the sleeve. The bottom wall has a dome-shaped upper surface which facilitates proper positioning and cutting action of the piercing spike. The spike is provided with an angularly-beveled cutting edge terminating at its lower end in a peripherally-disposed tip, has a lower portion of smaller external diameter than the upper portion thereof, and includes a separate airway for the introduction of filtered air into the bottle as its contents are drained. Because of an enlarged recess formed in the heel portion of the spike, insertion of the spike through the bottom wall of the closure results in the formation of a flap which is pushed aside (so that it does not obstruct liquid flow) but is not detached from the closure.

Other features, advantages, and objects of the invention will become apparent from the specification and drawings.

DRAWINGS

FIG. 1 is a perspective view of a closure and connector embodying this invention.

FIG. 2 is an enlarged vertical sectional view of the elements illustrated in FIG. 1, prior to coupling of the closure and connector.

FIG. 3 is a fragmentary sectional view of the parts depicted in FIG. 2 but showing such parts just as the closure is pierced.

FIG. 4 is a fragmentary sectional view similar to FIG. 3 but showing the connector fully inserted into the closure.

FIG. 5 is a fragmentary sectional view taken along line 5—5 of FIG. 4.

FIG. 6 is a fragmentary sectional view taken along line 6—6 of FIG. 4.

FIG. 7 is a fragmentary plan view taken along line 7—7 of FIG. 2.

FIG. 8 is a sectional view taken along line 8—8 of FIG. 2.

FIG. 9 is a fragmentary sectional view taken along line 9—9 of FIG. 2.

DESCRIPTION

Referring to the drawings, the numerals 10 and 11 generally designate the closure and connector, respectively, for the administration of surgical irrigation fluids. The closure 10 comprises a one-piece plastic cap having a cylindrical side wall 12, an annular top wall 13, a tubular sleeve 14 extending downwardly from the inside circumference of the top wall, and a bottom wall 15 closing the lower end of the sleeve. Since all of the walls are imperforate, the closure effectively seals the bottle 16 to which it is secured.

The bottle itself is conventional, being formed from glass, plastic, or any other suitable material in accordance with teachings and practices known in the art, and a detailed description of the bottle is therefore believed unnecessary here. It is to be noted, however, that the bottle is provided with a threaded neck 16a received within the annular space between side wall 12 and sleeve 14, and that the side wall is internally threaded for detachable connection to the bottle neck. Thus, when irrigating fluid is to be poured from the bottle, the closure is simply unthreaded from the neck in the usual manner.

The tubular sleeve 14 is spaced a substantial distance inwardly, not only from the inside surface of side wall 12 but also from the inner surface of neck 16a to which the side wall is threadedly connected. Such spacing is important because it accommodates outward flexure or stretching of the sleeve's tubular wall during a coupling operation as will be described more fully hereinafter.

The tubular sleeve is provided with an inwardly projecting annular rib 17 formed along its inner surface at a level adjacent to, but slightly below, the level of top wall 13. Below the rib, the inner surface 18 slopes or tapers gradually inwardly and downwardly so that the inside diameter of the sleeve at its lower end is less than the diameter of the opening defined by rib 17. An annular band or zone 19 of the inner surface, indicated by dashed lines in FIG. 2, encompasses that portion of inner surface 18 which has substantially the same inside diameter as rib 17. Above the rib, the sleeve is provided with an upwardly and outwardly flared upper surface 20 which not only helps to guide a connecting spike into the sleeve but also results in a reduced thickness of material at 21 where the sleeve merges with the top wall. Such reduced thickness contributes in permitting outward stretching or flexure of the sleeve in its primary sealing zone when a spike is forced into the sleeve as described below. While the angle of upper surface 20 may vary, it has been found that particularly effective results are achieved if the surface slopes upwardly and outwardly (or downwardly and inwardly) at an angle within the range of 40° to 70° when measured from the horizontal, the preferred range being approximately 60°.

Bottom wall 15 is dome-shaped in configuration and, in comparison with the other walls, is relatively thin, especially along its annular outer portion 15a which merges with the lower end of tubular sleeve 14. While the thickness of portion 15a may vary considerably depending upon the material used and the construction and composition of the piercing spike, it has been found that a minimum wall thickness of approximately 0.005 to 0.020 inches is effective if a high density polyethylene (having a density within the general range of 0.940 to 0.965 grams per cubic centimeter) is used. It is to be understood, of course, that other semi-rigid plastic materials having similar properties may be used in the fabrication of the closure. In addition to having good barrier properties and chemical inertness, the selected material should be relatively stiff (i.e., should have a stiffness modulus of at least 50,000 psi when measured by ASTM test method D747-63T), so that a secure threaded connection will be formed between the side wall 12 and bottle neck 16a, and should have sufficient heat resistance to withstand autoclaving temperatures (250° F.).

The dome shape of bottom wall 15 may be formed entirely in the molding operation, although it has been found that full development of the dome-shaped configuration may be obtained at least in part by increased pressure within bottle 16 when the sealed and filled bottle is subjected to sterilizing temperatures with cap 12 in place. Specifically, during such an autoclaving procedure, the thermoplastic material of the closure tends to soften, the bottom wall 15 assumes a fully-developed domed configuration as shown because of the increased internal pressure and also possibly because of limited shrinkage of the plastic, and upon cooling the plastic sets to retain the dome-shaped bottom wall configuration shown.

The connector 11 consists essentially of a handle or body portion 22 and a spike 23. The spike has a tubular wall 24 terminating at its lower end in an angular cutting edge 25. While the spike is illustrated as having single-bevel cutting edge, plural bevels may be provided as long as the cutting edge slopes generally upwardly from a peripherally-disposed tip portion 26 towards a diametrically-opposing heel portion 27. An enlarged recess 28 is formed in the heel, extending upwardly as shown in FIGS. 2, 5, and 8. A main passage 29 for the flow of irrigation fluid extends through the hollow spike and into the body portion, communicating with socket 30 which is in turn adapted to receive and retain the plug portion 31 of administration tube 32. The tube and its plug are entirely conventional and are therefore illustrated only in phantom. It is to be understood that the opposite end of the tube is adapted for connection to any of a variety of catheters, instruments, and other devices for the administration of irrigation fluids, and that if desired, the plug 31 may be eliminated and tube 32 may be joined directly to the connector 11.

An airway 33 also extends through the hollow spike and, as shown most clearly in FIGS. 2 and 8, is separate from main passage 29. The airway extends to the top portion 26 of the spike and, at its opposite end, communicates with a recess 34 in handle or body portion 22. A filter unit 35, containing a non-wetting microfilter of standard construction, is secured to the connector in flow communication with recess 34. The filter permits air, filtered for particulates and bacteria, to enter the bottle as its contents are drained without allowing liquid to escape through airway 33.

It is to be noted that the outside diameter of the upper portion 23a of the spike is substantially greater than the outside diameter of lower portion 23b. Specifically, upper portion 23a has outside dimensions slightly greater than the opening defined by annular rib 17 in sleeve 14. The lower portion 23b has a smaller outside diameter than the inside diameter of the rib, the spike's minimum outside diameter being the same or slightly less than the minimum inside diameter of the sleeve at the lower end thereof. It should be observed that the length of the spike substantially exceeds the length of sleeve 14 and, specifically, that the length of reduced lower portion 23b (measured from heel 27 to the upper end of portion 23b) exceeds the distance between rib 17 and bottom wall 15. In addition, the length of the enlarged upper cylindrical portion 23a exceeds the distance between rib 17 (the primary sealng zone) and the secondary lower sealing zone 19.

The body or handle portion of the spike preferably includes wing portions 22a which may be readily gripped to hold the connector between the fingers of one hand for driving the spike into fully seated position within the port sleeve of the closure. The body portion and spike of the connector are integrally formed of a rigid material. A rigid plastic such as polystyrene is preferred, although other plastic materials having similar properties of strength, rigidity, and hardness, or other materials such as metal, might be used. The rigidity or stiffness of the material of the connector 11 should be substantially greater that that of closure 10.

In operation, if the contents of the bottle are to be drained through an administration set, then any conventional protective cover (not shown) that may be provided over the entrance to the sleeve (to maintain the sterility of the surfaces thereof) is first removed and connector 11 of the administration set is then coupled to the closure by inserting spike 23 into the open-topped sleeve 14 in the manner illustrated in FIGS. 2-4. The reduced lower end portion 23b of the spike enters the sleeve and is freely slidable therein because of the greater internal dimensions of the sleeve. Tip 26 engages the periphery of bottom wall 15, piercing that wall and commencing the formation of an arcuate slit that extends about almost the entire periphery of that wall. Since the cutting edge 25 is interrupted at heel portion 27, the cutting action is similarly interrupted, resulting in the formation of a flap 36 which folds downwardly about hinge line 37 to make way for the descending spike (FIG. 3). The bottom wall therefore remains connected as flap 36 to the remainder of the closure and is not released into the body of fluid within the container. Furthermore, recess 28 enhances fluid drainage from the container and accentuates the separation of fluid removal from air entering via the air passageway 33. The benefit of this is a reduced tendency to entrap air bubbles in the mainstream at high flow rates, which bubbles, if carried all the way to the resectoscope or other instrument to which the administration tube is connected, might adversely affect the surgeon's view of the operative area.

Thereafter, following the piercing and cutting action, the enlarged upper portion 23a of the spike slidably and sealingly engages the primary sealing zone defined by annular rib 17 (FIGS. 4-6). Since the outside diameter of the spike's upper portion 23a is greater than the inside diameter of the upper sealing zone, slight outward flexure or stretching of the sleeve occurs in the vicinity of the rib. As already indicated, such outward displacement of the rib portion is aided by reason of the fact that the rib is spaced below the level of top wall 13 (i.e., below the undersurface thereof) and because of the reduced wall thickness at 21. Finally, the enlarged portion 23a of the spike enters into engagement with the inside surface of the sleeve at the secondary sealing zone 19, causing further outward flexure or stretching of the sleeve at that location (FIGS. 4-6). Positive and highly effective sealing between the connector and closure is thereby achieved. The gripping forces exerted by the stretched sleeve upon the spike are sufficiently great to prevent extraction of the spike when the bottle is inverted for administration and even when pulling forces of considerable magnitude are exerted upon the flexible tube.

During insertion of the spike into the port sleeve, should misalignment of the parts occur the flared upper surface 20 will tend to realign or center the spike. Furthermore, should the spike be introduced at an angle, the cooperative action between the outer surface of lower spike portion 23b, and the lateral sliding action which tends to occur as tip 26 engages the domed top surface of wall 15, results in automatic realignment of the descending spike.

Throughout the specification, closure 10 has been referred to as a "one-piece" closure to make it clear that the tubular port sleeve, which is piercable by and sealingly engagable with spike 23, is integral with top wall 13 and threaded side wall 12. It is to be understood, of course, that where the outer surface of the closure must be maintained in sterile condition, some outer cover (not shown) of any suitable or conventional design may be provided. Also, while the closure shown in the drawings is provided with a ribbed top wall 13 which sealingly engages the mouth of bottle 16, an annular resilient liner may if desired be interposed between the mouth and the underside of the top wall to contribute in forming an effective seal between the parts.

While in the foregoing an embodiment of the invention has been disclosed in considerable detail for purposes of illustration, it will be understood by those skilled in the art that many of these details may be varied without departing from the spirit and scope of the invention.

I claim:

1. A closure for fluid containers, said closure being formed of semi-rigid plastic material and having a generally cylindrical side wall, an annular top wall, a tubular sleeve extending downwardly from the inner perimeter of said top wall, and a bottom wall closing the lower end of said tubular sleeve, said tubular sleeve and said side, top and bottom walls being integrally formed of semi-rigid plastic material, said side wall having threads along the inner surface thereof for threadedly engaging the neck of a fluid container, said sleeve being substantially smaller in diameter than said side wall and having integral annular sealing means spaced below the level of said top wall.

2. The structure of claim 1 in which said sealing means comprises an inwardly projecting annular rib.

3. The structure of claim 2 in which said rib provides a primary sealing surface for sealingly engaging a connector spike insertable into said sleeve, said inner surface of said sleeve tapering downwardly and inwardly below said rib to define a secondary annular sealing zone spaced between said rib and said bottom wall and having a diameter no greater than the inside diameter of said rib.

4. The structure of claim 3 in which said secondary sealing zone defined by said tapered inner surface has substantially the same diameter as said rib.

5. The structure of claim 1 in which said bottom wall is dome-shaped.

6. The structure of claim 2 in which said sleeve is provided with an upper surface portion above said rib which slopes upwardly and outwardly at an angle within the range of 40° to 70° measured from the horizontal.

7. The structure of claim 2 in which said closure is one element of a two-element combination including a connector as the other element thereof, said connector comprising a handle and an integrally-formed spike, said spike having a tubular wall terminating at its lower end in a beveled cutting edge, said cutting edge sloping upwardly from a tip portion towards a heel portion of said spike, said spike having an upper portion with an outside diameter greater than the inside diameter of said rib.

8. The structure of claim 7 in which said spike includes a lower portion having an outside diameter smaller than the inside diameter of said rib.

9. The structure of claim 7 in which said tip and heel portions are diametrically opposed.

10. The structure of claim 7 in which said heel portion of said spike is provided with an upwardly-extending recess.

11. A one-piece closure for containers for surgical irrigation fluids and the like, said closure having a generally cylindrical side wall, an annular top wall, a tubular sleeve extending downwardly from the inner perimeter of said top wall, and a bottom wall closing the lower end of said sleeve, said side wall being internally threaded for threadedly engaging the neck of a fluid container and for removably retaining said closure in sealing relation therewith, said sleeve being of substantially smaller diameter than said side wall and providing a downwardly-tapered inner surface, said sleeve also having along the inner surface thereof a pair of spaced annular upper and lower zones for slidably and sealingly engaging a connector spike insertable into said sleeve, said upper zone being defined by an inwardly-projecting annular rib portion of said sleeve adjacent said top wall, said annular lower zone being disposed above said bottom wall and having a diameter no greater than the inside diameter of said rib.

12. The closure of claim 11 in which said lower zone comprises an annular portion of the tapered inner surface of said sleeve having substantially the same inside diameter as said rib.

13. The closure of claim 11 in which said rib is located below the level of the undersurface of said top wall.

14. The closure of claim 11 in which said bottom wall is dome-shaped.

15. The closure of claim 14 in which said dome-shaped bottom wall has a peripheral portion of reduced thickness, the thickness of said peripheral portion being within the range of 0.005 to 0.020 of an inch.

16. The structure of claim 11 in which said closure is formed of semi-rigid plastic material.

17. The structure of claim 16 in which said closure is formed of high density polyethylene.

18. The closure of claim 13 in which said sleeve is provided with an upper surface portion above said rib which slopes upwardly and outwardly at an angle within the range of 40° to 70° measured from the horizontal.

19. The structure of claim 11 in which said closure is one element of a two-element combination including a connector as the other element thereof, said connector comprising a handle and an integrally-formed spike, said spike having a tubular wall terminating at its lower end in a beveled cutting edge, said beveled cutting edge sloping upwardly from a tip portion towards a heel portion of said spike, said spike having an upper outer surface of a diameter slightly greater than the inside diameter of said upper and lower zones of said sleeve and being slidably engagable therewith.

20. The structure of claim 19 in which said spike includes a lower portion having an outside diameter substantially smaller than the inside diameter of said upper and lower annular zones of said sleeve.

21. The structure of claim 19 in which said heel portion of said spike is recessed.

22. A connector for coupling attachment to the closure of a solution bottle, said connector comprising a handle and spike formed integrally of rigid plastic material, said spike having a tubular wall terminating at its lower end in a beveled cutting edge, said cutting edge sloping upwardly from a tip portion towards a heel portion of said spike, said heel portion being provided with an upwardly-extending recess interrupting said cutting edge.

23. The structure of claim 22 in which said spike is provided with a lower portion extending upwardly from said tip and an upper portion interposed between said lower portion and said handle, said upper portion having a cylindrical outer surface of substantially greater diameter than said lower portion.

24. The connector of claim 22 in which said spike is provided with separate air and liquid passages extending therethrough, an opening for said air passage at the lower end of said spike being provided adjacent said tip portion and a separate opening for said liquid passage being disposed adjacent said recessed heel portion, whereby, the recess of said heel contributes in preventing air entering an inverted solution bottle from becoming entrained in liquid being drained from that bottle.

* * * * *